United States Patent
Perschbacher et al.

(10) Patent No.: US 11,207,536 B2
(45) Date of Patent: Dec. 28, 2021

(54) METHOD AND APPARATUS FOR ENHANCING ATRIAL FIBRILLATION DETECTION

(71) Applicant: Cardiac Pacemakers, Inc., St. Paul, MN (US)

(72) Inventors: David L. Perschbacher, Coon Rapids, MN (US); Sunipa Saha, Shoreview, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 50 days.

(21) Appl. No.: 16/737,711

(22) Filed: Jan. 8, 2020

(65) Prior Publication Data
US 2020/0215344 A1  Jul. 9, 2020

Related U.S. Application Data

(60) Provisional application No. 62/790,215, filed on Jan. 9, 2019.

(51) Int. Cl.
*A61N 1/39* (2006.01)
*A61B 5/361* (2021.01)

(52) U.S. Cl.
CPC .............. *A61N 1/395* (2013.01); *A61B 5/361* (2021.01); *A61N 1/3956* (2013.01)

(58) Field of Classification Search
None
See application file for complete search history.

(56) References Cited

U.S. PATENT DOCUMENTS 5,622,178 A   4/1997   Gilham
6,490,479 B2  12/2002  Bock
(Continued)

FOREIGN PATENT DOCUMENTS

AU   2015301633 B2   8/2018
CN      1829554 A    9/2006
(Continued)

OTHER PUBLICATIONS

"1.3.5.13. Runs Test for Detecting Nonrandomness", https://www.itl.nist.gov/div898/handbook/eda/section3/eda35d.htm, 2 pages, Oct. 31, 2018.
(Continued)

*Primary Examiner* — Paula J Stice
(74) *Attorney, Agent, or Firm* — Schwegman Lundberg & Woessner, P.A.

(57) ABSTRACT

An example of a system may include a sensing circuit and an atrial fibrillation (AF) detection circuit. The sensing circuit may be configured to sense a cardiac signal indicative of atrial and ventricular depolarizations. The AF detection circuit may be configured to detect AF using the cardiac signal and may include a detector and a detection enhancer. The detector may be configured to detect the ventricular depolarizations using the cardiac signal, to measure ventricular intervals each between two successively detected ventricular depolarizations, and to detect the AF using the ventricular intervals. The detection enhancer may include a respiratory sinus arrhythmia (RSA) detector configured to detect RSA using the cardiac signal and may be configured to verify each detection of the AF based on whether the RSA is detected.

20 Claims, 8 Drawing Sheets

(56) References Cited

U.S. PATENT DOCUMENTS

| | | |
|---|---|---|
| 6,491,639 B1 | 12/2002 | Turcott |
| 6,643,548 B1 | 11/2003 | Mai et al. |
| 6,931,273 B2 | 8/2005 | Groenewegen et al. |
| 7,031,765 B2 | 4/2006 | Ritscher et al. |
| 7,353,057 B2 | 4/2008 | Schiessle et al. |
| 7,412,282 B2 | 8/2008 | Houben |
| 7,596,405 B2 | 9/2009 | Kurzweil et al. |
| 7,657,307 B2 | 2/2010 | Van Dam et al. |
| 7,853,327 B2 | 12/2010 | Patangay et al. |
| 7,899,531 B1 | 3/2011 | Benser et al. |
| 8,195,280 B2 | 6/2012 | Van Dam et al. |
| 8,560,058 B2 | 10/2013 | Babaeizadeh et al. |
| 8,639,316 B2 | 1/2014 | Sarkar |
| 9,986,921 B2 | 6/2018 | Chon et al. |
| 9,999,359 B2 | 6/2018 | Thakur et al. |
| 9,999,368 B2 | 6/2018 | Perschbacher et al. |
| 10,194,820 B2 | 2/2019 | Thakur et al. |
| 10,485,442 B2 | 11/2019 | Krueger et al. |
| 2001/0034539 A1 | 10/2001 | Stadler et al. |
| 2002/0065473 A1 | 5/2002 | Wang et al. |
| 2004/0092836 A1 | 5/2004 | Ritscher et al. |
| 2004/0230129 A1 | 11/2004 | Haefner |
| 2005/0080347 A1 | 4/2005 | Sheth et al. |
| 2006/0247548 A1 | 11/2006 | Sarkar et al. |
| 2007/0100248 A1 | 5/2007 | Van Dam et al. |
| 2007/0142866 A1 | 6/2007 | Li |
| 2007/0149890 A1 | 6/2007 | Li et al. |
| 2008/0161703 A1 | 7/2008 | Houben et al. |
| 2009/0043218 A1 | 2/2009 | Warner et al. |
| 2009/0112110 A1 | 4/2009 | Zhang |
| 2010/0057152 A1 | 3/2010 | Kim et al. |
| 2010/0198285 A1 | 8/2010 | Rom |
| 2010/0241180 A1 | 9/2010 | Whitman et al. |
| 2010/0274149 A1 | 10/2010 | Li et al. |
| 2010/0331903 A1 | 12/2010 | Zhang et al. |
| 2011/0152957 A1 | 6/2011 | Shaquer |
| 2011/0224555 A1 | 9/2011 | Park |
| 2012/0035489 A1 | 2/2012 | Dong et al. |
| 2012/0101541 A1 | 4/2012 | Corbucci et al. |
| 2012/0238891 A1 | 9/2012 | Sarkar et al. |
| 2012/0238892 A1 | 9/2012 | Sarkar |
| 2012/0271186 A1 | 10/2012 | Siejko et al. |
| 2013/0150911 A1 | 6/2013 | Perschbacher et al. |
| 2013/0237872 A1 | 9/2013 | Zhang et al. |
| 2015/0164355 A1* | 6/2015 | Brockway .............. A61B 7/00 600/301 |
| 2015/0342466 A1 | 12/2015 | Thakur et al. |
| 2015/0342492 A1 | 12/2015 | Thakur et al. |
| 2016/0045125 A1 | 2/2016 | Krueger et al. |
| 2016/0287115 A1 | 10/2016 | Perschbacher et al. |
| 2017/0127965 A1 | 5/2017 | Krueger et al. |
| 2017/0277858 A1* | 9/2017 | Okubo .................. G16H 50/20 |
| 2018/0192902 A1 | 7/2018 | Perschbacher et al. |
| 2018/0242869 A1 | 8/2018 | Perschbacher et al. |
| 2018/0256053 A1 | 9/2018 | Perschbacher et al. |

FOREIGN PATENT DOCUMENTS

| | | |
|---|---|---|
| CN | 102176861 A | 9/2011 |
| CN | 106456023 A | 2/2017 |
| CN | 106659407 A | 5/2017 |
| CN | 107529988 A | 1/2018 |
| CN | 106456023 B | 3/2020 |
| EP | 2407097 A1 | 1/2012 |
| EP | 3277372 B1 | 8/2019 |
| JP | 2004524074 A | 8/2004 |
| JP | 2006524106 A | 10/2006 |
| JP | 2008539015 A | 11/2008 |
| JP | 2009089883 A | 4/2009 |
| JP | 2013535236 A | 9/2013 |
| JP | 2017527356 A | 9/2017 |
| JP | 2018511400 A | 4/2018 |
| JP | 6434129 B2 | 11/2018 |
| JP | 6525461 B2 | 5/2019 |
| WO | WO-2006118852 A2 | 11/2006 |
| WO | WO-2013020710 A1 | 2/2013 |
| WO | WO-2015088695 A1 | 6/2015 |
| WO | WO-2015187365 A1 | 12/2015 |
| WO | WO-2016025704 A1 | 2/2016 |
| WO | WO-2016160674 A1 | 10/2016 |
| WO | WO-2017079245 A1 | 5/2017 |
| WO | WO-2020146518 A1 | 7/2020 |

OTHER PUBLICATIONS

"U.S. Appl. No. 14/698,007, Corrected Notice of Allowance dated Feb. 9, 2018", 5 pgs.

"U.S. Appl. No. 14/698,007, Non Final Office Action dated Apr. 14, 2017", 7 pgs.

"U.S. Appl. No. 14/698,007, Notice of Allowance dated Jan. 18, 2018", 5 pgs.

"U.S. Appl. No. 14/698,007, Notice of Allowance dated Sep. 8, 2017", 5 pgs.

"U.S. Appl. No. 14/698,007, Response filed Mar. 6, 2017 to Restriction Requirement dated Jan. 6, 2017", 11 pgs.

"U.S. Appl. No. 14/698,007, Restriction Requirement dated Jan. 6, 2017", 6 pgs.

"U.S. Appl. No. 14/717,342, Final Office Action dated Jun. 6, 2018", 10 pgs.

"U.S. Appl. No. 14/717,342, Non Final Office Action dated Jun. 2, 2017", 8 pgs.

"U.S. Appl. No. 14/717,342, Non Final Office Action dated Nov. 27, 2017", 8 pgs.

"U.S. Appl. No. 14/717,342, Notice of Allowance dated Sep. 20, 2018", 7 pgs.

"U.S. Appl. No. 14/717,342, Response filed Jan. 30, 2018 to Non Final Office Action dated Nov. 27, 2017", 12 pgs.

"U.S. Appl. No. 14/717,342, Response filed Jul. 17, 2017 to Non Final Office Action dated Jun. 2, 2017", 12 pgs.

"U.S. Appl. No. 14/717,342, Response filed Jul. 23, 2018 to Final Office Action dated Jun. 6, 2018", 12 pgs.

"U.S. Appl. No. 14/717,342, Restriction Requirement dated Dec. 27, 2016", 10 pgs.

"U.S. Appl. No. 14/825,669, Response filed Apr. 24, 2017 to Final Office Action dated Mar. 9, 2017", 12 pgs.

"U.S. Appl. No. 14/825,669, Advisory Action dated May 3, 2017", 3 pgs.

"U.S. Appl. No. 14/825,669, Appeal Brief filed Dec. 26, 2017", 17 pgs.

"U.S. Appl. No. 14/825,669, Final Office Action dated Mar. 9, 2017", 13 pgs.

"U.S. Appl. No. 14/825,669, Non Final Office Action dated Jun. 23, 2017", 9 pgs.

"U.S. Appl. No. 14/825,669, Response filed Jun. 8, 2017 to Final Office Action dated Mar. 9, 2017", 14 pgs.

"U.S. Appl. No. 15/082,440, Corrected Notice of Allowance dated Feb. 9, 2018", 5 pgs.

"U.S. Appl. No. 15/082,440, Examiner Interview Summary dated Sep. 6, 2017", 2 pgs.

"U.S. Appl. No. 15/082,440, Non Final Office Action dated Jun. 21, 2017", 9 pgs.

"U.S. Appl. No. 15/082,440, Notice of Allowance dated Jan. 18, 2018", 8 pgs.

"U.S. Appl. No. 15/082,440, Notice of Allowance dated Sep. 25, 2017", 10 pgs.

"U.S. Appl. No. 15/082,440, Response filed May 17, 2017 to Restriction Requirement dated Mar. 30, 2017", 9 pgs.

"U.S. Appl. No. 15/082,440, Response filed Sep. 5, 2017 to Non Final Office Action dated Jun. 21, 2017", 14 pgs.

"U.S. Appl. No. 15/082,440, Restriction Requirement dated Mar. 30, 2017", 7 pgs.

"U.S. Appl. No. 15/341,565, Non Final Office Action dated Mar. 6, 2019", 12 pgs.

"U.S. Appl. No. 15/341,565, Notice of Allowance dated Jul. 26, 2019", 8 pgs.

"U.S. Appl. No. 15/341,565, Response filed Jun. 6, 2019 to Non Final Office Action dated Mar. 6, 2019", 10 pgs.

(56) References Cited

OTHER PUBLICATIONS

"U.S. Appl. No. 15/341,565, Response filed Dec. 10, 2018 to Restriction Requirement dated Oct. 15, 2018", 8 pgs.
"U.S. Appl. No. 15/341,565, Restriction Requirement dated Oct. 15, 2018", 6 pgs.
"U.S. Appl. No. 15/967,326, Advisory Action dated Mar. 14, 2019", 3 pgs.
"U.S. Appl. No. 15/967,326, Final Office Action dated Jan. 3, 2019", 11 pgs.
"U.S. Appl. No. 15/967,326, Final Office Action dated Aug. 7, 2019", 6 pgs.
"U.S. Appl. No. 15/967,326, Non Final Office Action dated Apr. 18, 2019", 9 pgs.
"U.S. Appl. No. 15/967,326, Non Final Office Action dated Jun. 29, 2018", 9 pgs.
"U.S. Appl. No. 15/967,326, Notice of Allowance dated Sep. 16, 2019", 7 pgs.
"U.S. Appl. No. 15/967,326, Response filed Feb. 21, 2019 to Final Office Action dated Jan. 3, 2019", 11 pgs.
"U.S. Appl. No. 15/967,326, Response filed Jul. 18, 2019 to Non Final Office Action dated Apr. 18, 2019", 8 pgs.
"U.S. Appl. No. 15/967,326, Response filed Aug. 20, 2019 to Final Office Action dated Aug. 7, 2019", 8 pgs.
"U.S. Appl. No. 15/967,326, Response filed Sep. 24, 2018 to Non Final Office Action dated Jun. 29, 2018", 13 pgs.
"U.S. Appl. No. 14/717,342, Response filed Feb. 16, 2017 to Restriction Requirement dated Dec. 27, 2016", 9 pgs.
"Australian Application Serial No. 2015301633, First Examiners Report dated Sep. 7, 2017", 3 pgs.
"Australian Application Serial No. 2015301633, Response filed Mar. 21, 2018 to First Examiners Report dated Sep. 7, 2017", 14 pgs.
"Chinese Application Serial No. 201580030296.4, Office Action dated Aug. 28, 2019", w/ English Translation, 13 pgs.
"Chinese Application Serial No. 201580030296.4, Office Action dated Dec. 28, 2018", W/ English Translation, 13 pgs.
"Chinese Application Serial No. 201580030296.4, Response filed Apr. 25, 2019 to Office Action dated Dec. 28, 2018", w/ English claims, 17 pgs.
"Chinese Application Serial No. 201580030296.4, Response filed Oct. 28, 2019 to Office Action dated Aug. 28, 2019", w/ English Claims, 8 pgs.
"Chinese Application Serial No. 201580047246.7, Office Action dated Mar. 6, 2019", w/ English Translation, 19 pgs.
"Chinese Application Serial No. 201580047246.7, Office Action dated Sep. 19, 2019", W/ English Translation, 10 pgs.
"Chinese Application Serial No. 201580047246.7, Response Filed Jul. 22, 2019 to Office Action dated Mar. 6, 2019", w/English Claims, 17 pgs.
"European Application Serial No. 15727196.6, Response filed Aug. 2, 2017 to Communication Pursuant to Rules 161(2) and 162 EPC dated Jan. 27, 2017", 7 pgs.
"European Application Serial No. 15757059.9, Response filed Sep. 26, 2017 to Communication Pursuant to Rules 161(1) and 162 EPC dated Mar. 21, 2017", 18 pgs.
"European Application Serial No. 16715709.8, Response filed Jun. 27, 2018 to Communication Pursuant to Rules 161(1) and 162 EPC dated Dec. 7, 2017", 28 pgs.
"International Application Serial No. PCT/US2015/031703, International Preliminary Report on Patentability dated Dec. 15, 2016", 10 pgs.
"International Application Serial No. PCT/US2015/045042, International Preliminary Report on Patentability dated Feb. 23, 2017", 10 pgs.
"International Application Serial No. PCT/US2015/045042, International Search Report dated Oct. 27, 2015", 6 pgs.
"International Application Serial No. PCT/US2015/045042, Written Opinion dated Oct. 27, 2015", 9 pgs.
"International Application Serial No. PCT/US2015/31703, International Search Report dated Sep. 22, 2015", 4 pgs.
"International Application Serial No. PCT/US2015/31703, Written Opinion dated Sep. 22, 2015", 8 pgs.
"International Application Serial No. PCT/US2016/024463, International Preliminary Report on Patentability dated Oct. 12, 2017", 8 pgs.
"International Application Serial No. PCT/US2016/024463, International Search Report dated Jun. 17, 2016", 6 pgs.
"International Application Serial No. PCT/US2016/024463, Written Opinion dated Jun. 17, 2016", 6 pgs.
"International Application Serial No. PCT/US2016/060050, International Preliminary Report on Patentability dated May 17, 2018", 7 pgs.
"International Application Serial No. PCT/US2016/060050, International Search Report dated Feb. 6, 2017", 4 pgs.
"International Application Serial No. PCT/US2016/060050, Written Opinion dated Feb. 6, 2017", 5 pgs.
"Japanese Application Serial No. 2017-508064, Office Action dated Mar. 6, 2018", With English Translation, 4 pgs.
"Japanese Application Serial No. 2017-508064, Response filed May 30, 2018 to Office Action dated Mar. 6, 2018", w/ English claims, 10 pgs.
"Japanese Application Serial No. 2017-550731, Notification of Reasons for Refusal dated Dec. 18, 2018", w/ English summary, 6 pgs.
"Japanese Application Serial No. 2017-550731, Office Action dated Sep. 4, 2018", w/ English translation (machine), 8 pgs.
"Japanese Application Serial No. 2017-550731, Response filed Mar. 15, 2019 to Notification of Reasons for Refusal dated Dec. 18, 2018", w/ English claims, 6 pgs.
"Japanese Application Serial No. 2017-550731, Response filed Nov. 28, 2018 to Office Action dated Sep. 4, 2018", w/ English claims, 8 pgs.
Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.
Esperer, et al., "Cardiac arrhythmias imprint specific signatures on Lorenz plots", Ann Noninvasive Electrocardiol, (2008), 44-60 pgs.
Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.
Tateno, K, et al., "Automatic detection of atrial fibrillation using the coefficient of variation and density histograms of RR and ?RR intervals", Medical and Biological Engineering and Computing, vol. 39, No. 6,, (Nov. 30, 2001), 664-671.
Thakur, Pramodsingh Hirasingh, et al., "System and Methods for Detecting Atrial Tachyarrhythmia Using Hemodynamic Sensors", U.S. Appl. No. 62/004,481, filed May 29, 2014.
"European Application Serial No. 15727196.6, Communication Pursuant to Article 94(3) EPC dated Jun. 30, 2020", 4 pgs.
"European Application Serial No. 15727196.6, Response filed Nov. 3, 2020 to Communication Pursuant to Article 94(3) EPC dated Jun. 30, 2020", 21 pgs.
"International Application Serial No. PCT/US2020/012768, International Preliminary Report on Patentability dated Jul. 22, 2021", 11 pgs.
"International Application Serial No. PCT/US2020/012768, International Search Report dated Mar. 25, 2020", 4 pgs.
"International Application Serial No. PCT/US2020/012768, Written Opinion dated Mar. 25, 2020", 8 pgs.
Chandler, et al., "Is respiratory sinus arrhythmia present in atrial fibrillation? A study using two quantitative methods", Medical Engineering & Physics, Butterworth Heinemann, GB, vol. 16, No. 4, (Jul. 1, 1994), 334-337.
Stacy, Westerman B, et al., "The subcutaneous implantable cardioverter defibrillator—review of the recent data", Journal of geriatric cardiology : JGC, (Mar. 28, 2018), 222-228.

* cited by examiner

METHOD AND APPARATUS FOR ENHANCING ATRIAL FIBRILLATION DETECTION

CLAIM OF PRIORITY

This application claims the benefit of priority under 35 U.S.C. § 119(e) of U.S. Provisional Patent Application Ser. No. 62/790,215, filed on Jan. 9, 2019, which is herein incorporated by reference in its entirety.

TECHNICAL FIELD

This document relates generally to cardiac rhythm management and more particularly to method and apparatus for enhancing atrial fibrillation (AF) detection by reducing false positive errors related to respiratory sinus arrhythmia (RSA).

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract at a normal sinus rate.

Tachyarrhythmia occurs when the heart contracts at a rate higher than the normal sinus rate. Tachyarrhythmia generally includes ventricular tachyarrhythmia (VT) and supraventricular tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT can be physiologic (e.g., sinus tachycardia) or pathologic (e.g., atrial fibrillation). The physiologic sinus tachycardia occurs when the SA node generates the electrical impulses at a particularly high rate. A pathologic SVT occurs, for example, when a pathologic conduction loop forms in an atrium or both atria. Fibrillation occurs when the heart contracts at a tachyarrhythmic rate with an irregular rhythm. Ventricular fibrillation (VF), as a ventricular arrhythmia with an irregular conduction, is a life-threatening condition requiring immediate medical treatment such as ventricular defibrillation. Atrial fibrillation (AF), as an SVT with an irregular rhythm, though not directly life threatening, also needs medical attention for purposes such as assessing a patient's cardiovascular conditions, atrial defibrillation, and/or adjusting other therapies received by the patient to restore cardiovascular functions and/or to prevent the deterioration of the heart.

SUMMARY

An example (e.g., "Example 1") of a system may include a sensing circuit and an atrial fibrillation (AF) detection circuit. The sensing circuit may be configured to sense a cardiac signal indicative of atrial and ventricular depolarizations. The AF detection circuit may be configured to detect AF using the cardiac signal and may include a detector and a detection enhancer. The detector may be configured to detect the ventricular depolarizations using the cardiac signal, to measure ventricular intervals each between two successively detected ventricular depolarizations, and to detect the AF using the ventricular intervals. The detection enhancer may include a respiratory sinus arrhythmia (RSA) detector configured to detect RSA using the cardiac signal and may be configured to verify each detection of the AF based on whether the RSA is detected.

In Example 2, the subject matter of Example 1 may optionally be configured such that the detector is configured to compute a measure of ventricular rate variability using the ventricular intervals and to indicate a suggested detection of the AF in response the measure of ventricular rate variability satisfying one or more criteria for the AF, and the detection enhancer is configured to indicate a detection of the AF in response to the suggested detection of the AF being indicated while the RSA is not detected.

In Example 3, the subject matter of any one or any combination of Examples 1 and 2 may optionally be configured such that the detection enhancer is configured to negate a detection of the AF when the RSA is detected.

In Example 4, the subject matter of any one or any combination of Examples 1 to 3 may optionally be configured such that the detection enhancer is configured to indicate a false positive detection of the AF when the AF is detected by the detector while the RSA is detected.

In Example 5, the subject matter of any one or any combination of Examples 1 to 4 may optionally be configured such that the RSA detector includes a runs detector and a runs analyzer. The runs detector is configured to detect runs of consecutively faster heart beats and consecutively slower heart beats from the cardiac signal over a period. The runs analyzer configured to analyze the detected runs for an RSA pattern and to declare a detection of the RSA in response to the RSA pattern being present.

In Example 6, the subject matter of Example 5 may optionally be configured such that the runs analyzer is configured to produce a histogram of percentage of runs having each number of heart beats plotted against a duration of runs specified by a number of heart beats.

In Example 7, the subject matter of Example 6 may optionally be configured such that the runs analyzer is configured to detect the RSA pattern including at least one of a substantially low percentage of 1-beat runs or an increasing number of multiple-beat runs as the number of beats in each of the multiple-beat runs increases.

In Example 8, the subject matter of any one or any combination of Examples 1 to 7 may optionally be configured to include an implantable medical device including the sensing circuit and the AF detection circuit.

In Example 9, the subject matter of Example 8 may optionally be configured such that the sensing circuit is configured to sense a ventricular electrogram.

In Example 10, the subject matter of Example 8 may optionally be configured such that the sensing circuit is configured to sense a subcutaneous electrocardiogram.

In Example 11, the subject matter of Example 8 may optionally be configured such that the implantable medical device includes an implantable loop recorder.

In Example 12, the subject matter of any one or any combination of Examples 1 to 11 may optionally be configured to further include a therapy device and a therapy control circuit. The therapy device is configured to deliver one or more therapies. The therapy control circuit is configured to control the delivery of the one or more therapies based on whether each detection of the AF is verified.

In Example 13, the subject matter of Example 12 may optionally be configured such that the implantable medical device includes a subcutaneous implantable cardioverter defibrillator.

In Example 14, the subject matter of Example 12 may optionally be configured such that the implantable medical device includes a ventricular implantable cardioverter defibrillator.

In Example 15, the subject matter of any one or any combination of Examples 1 to 14 may optionally be configured to further include a storage device and a storage control circuit. The storage device is configured to store portions the sensed cardiac signal. The storage control circuit is configured to start storage of a portion of the portions of the sensed cardiac signal in response to each detection of the AF being verified.

An Example (e.g., "Example 16") of a method is also provided. The method may include sensing a cardiac signal indicative of atrial and ventricular depolarizations, detecting the ventricular depolarizations using the cardiac signal, measuring ventricular intervals each between two successively detected ventricular depolarizations, detecting atrial fibrillation (AF) using the ventricular intervals, detecting respiratory sinus arrhythmia (RSA) using the cardiac signal, and verifying each detection of the AF based on whether the RSA is detected.

In Example 17, the subject matter of detecting the AF using the ventricular intervals as found in Example 16 may optionally include computing a measure of ventricular rate variability using the ventricular intervals and indicating a suggested detection of AF in response the measure of ventricular rate variability satisfying one or more criteria for AF, and the subject matter of verifying each detection of the AF as found in Example 16 may optionally include indicating a detection of the AF in response to the suggested detection of the AF being indicated while the RSA is not detected.

In Example 18, the subject matter of any one or any combination of Examples 16 and 17 may optionally further include negating a detection of the AF when the RSA is detected.

In Example 19, the subject matter of any one or any combination of Examples 16 to 18 may optionally further include indicating a false positive detection of the AF when the AF is detected by the detector while the RSA is detected.

In Example 20, the subject matter of any one or any combination of Examples 16 to 19 may optionally further include triggering storage of the sensed cardiac signal in response to the each detection of the AF being verified.

In Example 21, the subject matter of detecting the RSA as found in any one or any combination of Examples 16 and 17 and may optionally further include detecting runs of consecutively faster heart beats and consecutively slower heart beats from the cardiac signal over a period, analyzing the detected runs for an RSA pattern, and declaring a detection of the RSA in response to the RSA pattern being present.

In Example 22, the subject matter of analyzing the detected runs for the RSA pattern as found in Example 21 may optionally include producing a histogram of percentage of runs having each number of heart beats plotted against a duration of runs specified by a number of heart beats and detecting the RSA pattern including at least one of a substantially low percentage of 1-beat runs or an increasing number of multiple-beat runs as the number of beats in each of the multiple-beat runs increases.

In Example 23, the subject matter of sensing the cardiac signal as found in any one or any combination of Examples 16 to 22 may optionally include sensing a subcutaneous electrocardiogram from a site remote from a heart.

In Example 24, the subject matter of any one or any combination of Examples 16 to 23 may optionally further include delivering one or more therapies and controlling the delivery of the one or more therapies based on whether the each detection of the AF is verified.

In Example 25, the subject matter of delivering the one or more therapies as found in any one or any combination of Example 24 may optionally include delivering at least one of the one or more therapies from an implantable medical device.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
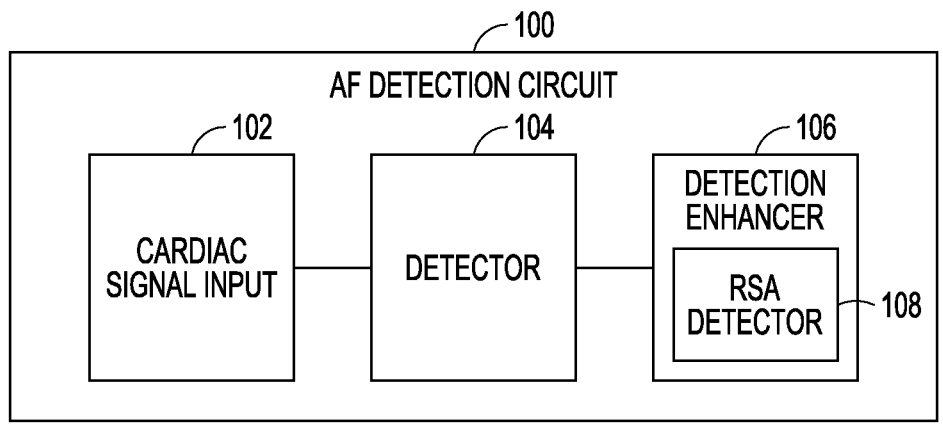
FIG. 1 is a block diagram illustrating an embodiment of an atrial fibrillation (AF) detection circuit.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for detecting atrial fibrillation (AF, also referred to as "AFib"). Existing methods for detecting AF include algorithms based on ventricular rate variability (or ventricular cycle length variability, also referred to as R-R variability or V-V variability), which is a measure of the beat-to-beat variance in ventricular intervals (time interval between two successive ventricular depolarizations, or R-waves). Such methods, however, may give false-positive errors sometimes due to variations in the ventricular rate not resulting from variations in the atrial rate. With devices such as insertable cardiac monitors and ventricular defibrillators that have no electrical access to the right atrium, atrial activities may not be directly detectable for enhancing AF detection. False positive AF detection may occur due to naturally occurring phenomena which result in an unstable ventricular heart rate. Examples of such phenomena include premature atrial contractions (PACs), premature ventricular contractions (PVCs), Wenckebach phenomenon (second degree atrioventricular block, Mobitz I), and respiratory sinus arrhythmia (RSA). False positive AF detections by devices increase workload for physicians and clinic staff responding to and reviewing the resulting alerts.

The present system detects AF using ventricular intervals and excludes false positive detections by detecting RSA. RSA is heart rate variability in synchrony with respiration, by which the ventricular cycle length (also referred to as R-R interval or V-V interval) on an electrocardiogram (ECG) is shortened during inspiration and prolonged during expiration. By detecting RSA and preventing a device from declaring an AF detection while RSA is being detected, the present system reduces false positive AF detections associated with RSA. In various embodiments, RSA can be detected alone or in combination with detection of other one or more phenomena to reduce the false positive error rate in AF detection. In various embodiments, a programmable option to enable automatic discrimination of AF using RSA is provided to selected patients.

RSA may also be indicated by cyclical amplitude variation in an ECG signal. This allows for detection of both AF and RSA using a single ECG signal. Depending on the need and the application, the detections can be performed by a device implanted in or otherwise worn by the patient and/or a remote server communicating to the device. In various embodiments, a statistical runs test may determine whether ventricular cycle length (V-V interval) variation in a particular data set is from a random process or a non-random, cyclic process such as RSA.

In various embodiments, the AF detection is performed for diagnostic and/or therapeutic purposes. In an embodiment, a verified AF detection may trigger storage of a cardiac signal for monitoring and diagnosing of arrhythmic conditions in a patient, and the storage may continue until AF is no longer detected or verified. In another embodiment, delivery of a therapy to a patient may be started, stopped, or adjusted in response to a verified AF detection. While some specific devices are discussed in this document as examples, the present system and method may be employed in any device and system where AF is to be detected.

The relationship between a heart rate and a cardiac interval (also known as cardiac cycle length), as used in this document, is the relationship between a frequency and its corresponding period. If a heart rate is given in beats per minute (bpm), its corresponding cardiac interval in milliseconds is calculated by dividing 60,000 by the heart rate (where 60,000 is the number of milliseconds in a minute). Any process, such as a comparison, using a heart rate is to be modified accordingly when a cardiac interval is used instead. Examples of the heart rate include atrial rate and ventricular rate. Examples of the cardiac interval (or cycle length) include atrial interval (or cycle length) and ventricular interval (or cycle length).

In this document, a "user" includes a physician or other caregiver who examines and/or treats a patient using one or more of the methods and apparatuses reported in the present document.

FIG. 1 is a block diagram illustrating an embodiment of an AF detection circuit 100. AF detection circuit 100 can include a cardiac signal input 102, a detector 104, and a detection enhancer 108. AF detection circuit 100 can detect AF using a cardiac signal indicative of atrial and ventricular depolarizations.

Cardiac signal input 102 receives the cardiac signal indicative of atrial and ventricular depolarizations. In various embodiments, the cardiac signal may include a single signal indicative of both atrial and ventricular depolarizations or multiple signals each indicative of at least one of the atrial depolarizations and ventricular depolarizations.

Detector 104 can be configured to detect the ventricular depolarizations (R-waves) using the cardiac signal, to measure ventricular intervals (R-R intervals) each between two successively detected ventricular depolarizations, and to detect AF using the ventricular intervals. In one embodiment, detector 104 computes a measure of ventricular rate variability using the ventricular intervals and indicates a suggested detection of AF in response the measure of ventricular rate variability satisfying one or more criteria for AF. The ventricular rate variability (or ventricular cycle length variability, also referred to as the R-R variability or V-V variability) corresponds to heart rate variability (HRV) measured over a relatively short period. In one embodiment, detector 104 measures the ventricular intervals each associated with a detected ventricular depolarization and determines the ventricular rate variability as the beat-to-beat variance in the ventricular intervals over a specified number of heart beats or over a specified time interval. Examples of AF detection using ventricular rate variability are discussed in U.S. Patent No. 11,051,746, entitled "ATRIAL FIBRILLATION DETECTION USING VENTRICULAR RATE VARIABILITY", and U.S. Pat. No. 9,999,368, entitled "ATRIAL FIBRILLATION DETECTION", both assigned to Cardiac Pacemakers, Inc., which are incorporated herein by reference in their entirety.

The heart rate is rhythmic and varies with respiration. The heart rate may appear very unstable using heart rate variability/stability measurements, and therefore may lead to false positive detection of AF. The present subject matter can reduce such false positive detection of AF associated with RSA. Detection enhancer 108 can include an RSA detector 108 to detect RSA using the cardiac signal and can verify the detection of the AF based on whether the RSA is detected. A detection of AF, such as the suggested detection of AF, is verified when the AF is not detected while the RSA is detected. Detection enhancer 108 can indicate a detection of AF in response to the suggested detection of the AF being indicated while the RSA is not detected. When the RSA is detected, detection enhancer 108 can mark the detection of AF as a false positive detection and/or negate the detection of AF.

Figure 2:
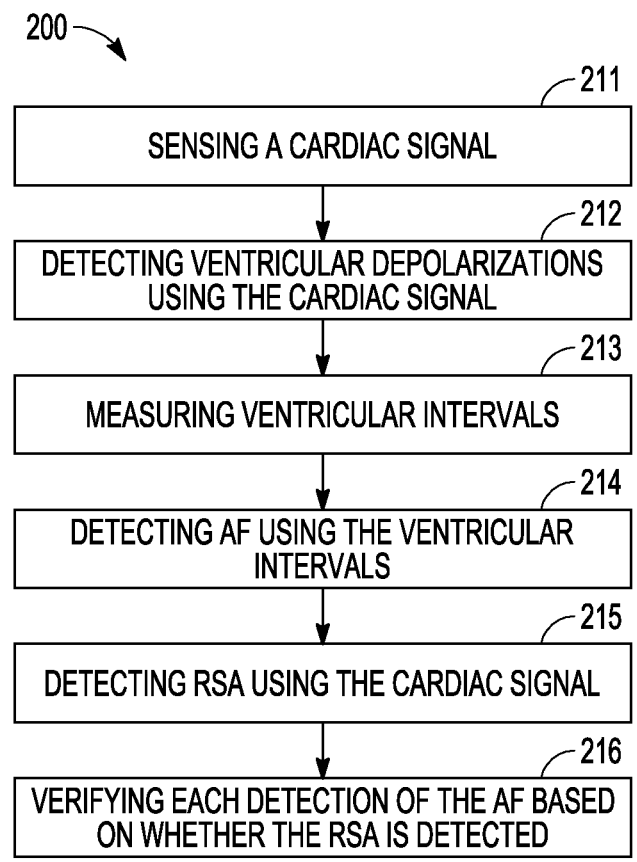
FIG. 2 is a flow chart illustrating an embodiment of a method for detecting AF.

FIG. 2 is a flow chart illustrating an embodiment of a method 210 for detecting AF. In one embodiment, AF detection circuit 100 is configured to perform method 210. For example, detector 104 can be configured to perform steps 212-214, and detection enhancer 108 can be configured to perform steps 215 and 216.

At 211, a cardiac signal is sensed. At 212, ventricular depolarizations are detected from the sensed cardiac signal. At 213, ventricular intervals are measured. At 214, AF is detected using the ventricular intervals. In various embodiments, a parameter representative of ventricular rate variability is computed using the ventricular intervals, and the AF is detected based on that parameter. A suggested detection of the AF can be indicated in response to the detection of the AF based on the parameter.

At 215, RSA is detected using the sensed cardiac signal. At 216, each detection of the AF is verified based on whether the RSA is detected. A detection of the AF is indicated in response to the suggested detection of the AF being indicated while the RSA is not detected. When the suggested detection of the AF is indicated while the RSA is detected, the detection of the AF is negated, and/or a false positive detection of the AF is indicated. In various embodiments, storage of data representing a detection of the AF and a portion of the cardiac signal associated with the detected AF is triggered in response to the detection of the AF being verified.

Figure 3:
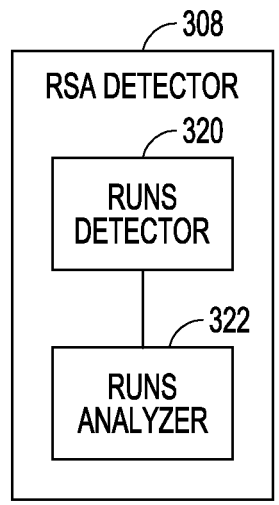
FIG. 3 is a block diagram illustrating an embodiment of a respiratory sinus arrhythmia (RSA) detector that can be used to enhance AF detection, such as in the AF detection circuit of FIG. 1.

FIG. 3 is a block diagram illustrating an embodiment of an RSA detector 308 that can be used to enhance AF detection. RSA detector 308 can represent an example of RSA 108 and can include a runs detector 320 and a runs analyzer 322. While detection of RSA using a statistical runs test is discussed as an example, the detection of RSA for verifying detection of AF according to the present subject matter is not limited to using the statistical runs test, but can use any method suitable for detecting RSA.

The statistical runs test determines whether a set of data represents a random process. A run is a series of increasing values or a series of decreasing values in the set of data. The number of the increasing or decreasing values is the duration of the run. The basis for the runs test is that in a set of random data, the probability of the next value being larger or smaller follows a binomial distribution. The statistical runs test is discussed in NIST/SEMATECH e-Handbook of Statistical Methods, www.itl.nist.gov, 2013. RSA detector 308, including runs detector 320 and runs analyzer 322, can be configured to detect RSA using such a runs test.

Runs detector 320 can detect runs of consecutively faster beats and consecutively slower beats over a period. The consecutively faster beats are consecutive heart beats with increasing cardiac cycle lengths. The consecutively slower beats are consecutive heart beats with decreasing cardiac cycle lengths. In various embodiments, the period can be specified between 30 seconds and 24 hours, with 2, 6, and 10 minutes being specific examples.

Runs analyzer 322 can analyze the detected runs for an RSA pattern and declare detection of the RSA in response to the RSA pattern being present. The RSA pattern includes a non-random, cyclic pattern of the ventricular rate or cycle length. The RSA is detected when runs analyzer 322 determines that the non-random, cyclic pattern of the ventricular rate or cycle length is present. In various embodiments, runs analyzer 322 can detect the RSA pattern from a histogram of percentage of runs plotted against run durations (number of beats per run). The RSA pattern can be characterized by low percentage of 1-beat runs and/or substantially increasing numbers of longer runs. In various embodiment, runs analyzer 322 can detect the RSA pattern when the percentage of 1-beat runs is below a specified threshold percentage and/or an increasing trend in the number of multiple-beat runs as the number of beats in one or more of the multiple-beat runs increases is present. The increasing trend is present when the number of multiple-beat runs substantially increases with an increasing number of beats in one or more of the multiple-beat runs. The threshold percentage for the 1-beat runs can be specified between 1% and 50%, with 30, 35, and 40% being specific examples. The "increasing trend" or "substantially increasing" means that as the number of beats in each of the multiple-beat runs increases (e.g., from 3-beat runs to 4-beat runs), the number (or percentage) of runs increases or remains unchanged (e.g., five 3-beat runs and ten or more 4-beat runs). The number can be specified between 1 and 1,000, with 0, 5, and 10 being specific examples, or the absolute percentage can be specified between 0% and 99%, with 5%, 10%, and 20% being specific examples. The percentage can also be specified as a relative percentage increase (e.g. 25% more 4-beat runs than 3-beat runs).

Figure 4:
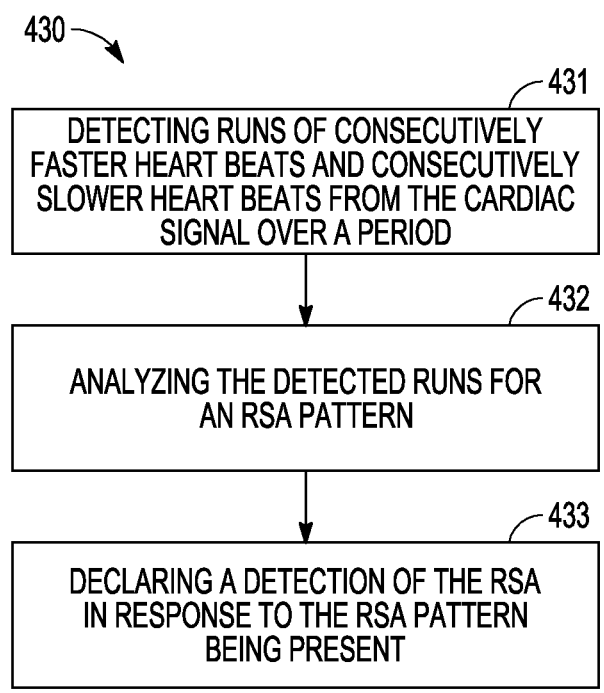
FIG. 4 is a flow chart illustrating an embodiment of a method for detecting RSA that can be used in a method for detecting AF, such as the method of FIG. 2.

FIG. 4 is a flow chart illustrating an embodiment of a method 430 for detecting RSA that represent an example, but not a limitation, of how step 215 in method 210 can be performed. In one embodiment, RSA detector 308 is configured to perform method 430. For example, runs detector 320 can be configured to perform step 431, and runs analyzer 322 can be configured to perform steps 432 and 433.

Figure 5A:
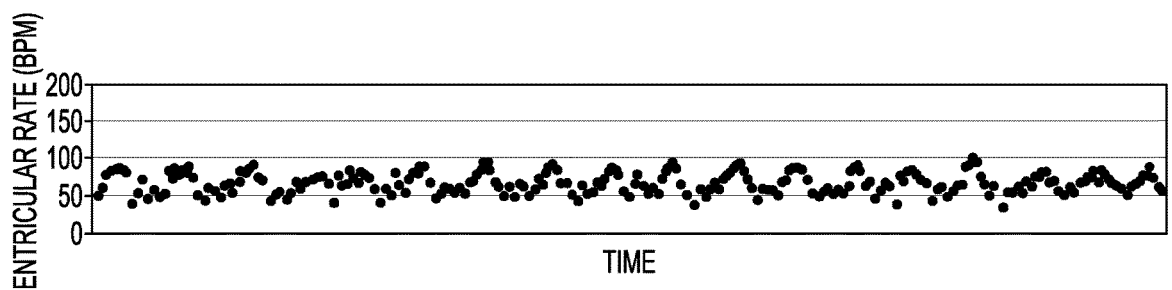
FIG. 5A is a graph showing an example of heart rate varying with respiration.

At 431, runs of consecutively faster heart beats and consecutively slower heart beats are detected from a cardiac signal over a period. At 432, the detected runs are analyzed for an RSA pattern. At 433, a detection of the RSA is declared in response to the RSA pattern being present. FIG. 5A is a graph showing an example of RSA, in which the ventricular rate is rhythmic and varies with respiration. In various embodiments, the RSA pattern can be detected from a histogram of percentage of runs plotted against run durations (number of beats per run). The RSA pattern can be detected by detecting a non-random, cyclic pattern of the ventricular rate as indicated by the histogram. For example, the RSA pattern can be detected in response to the percentage of 1-beat runs being below a specified percentage or presence of an increasing number of multiple-beat runs as the number of beats in each of the multiple-beat runs increases. Examples of such histograms are shown in FIGS. 5B-F.

Figure 5B:
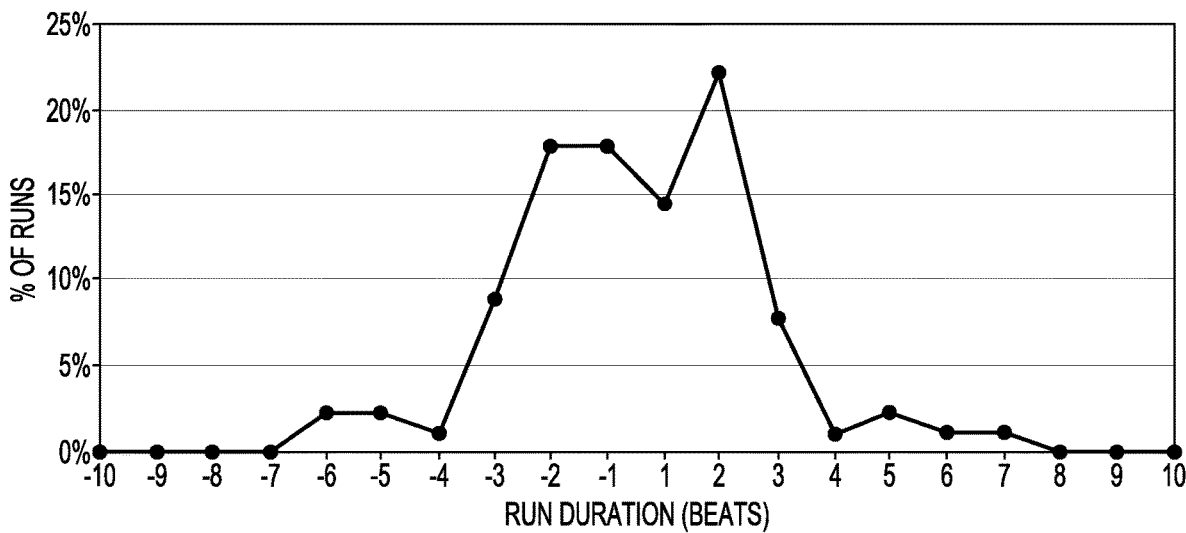
FIGS. 5B-G are histograms illustrating various examples of runs distribution in RSA detection using the method of FIG. 4.
Figure 5C:
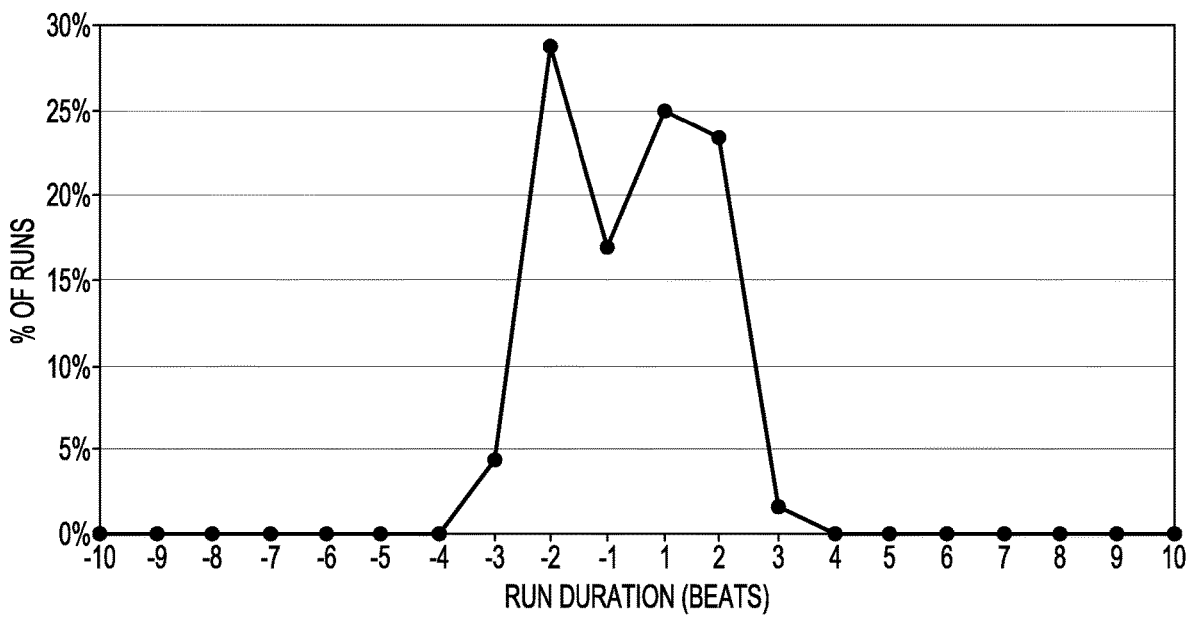
Figure 5D:
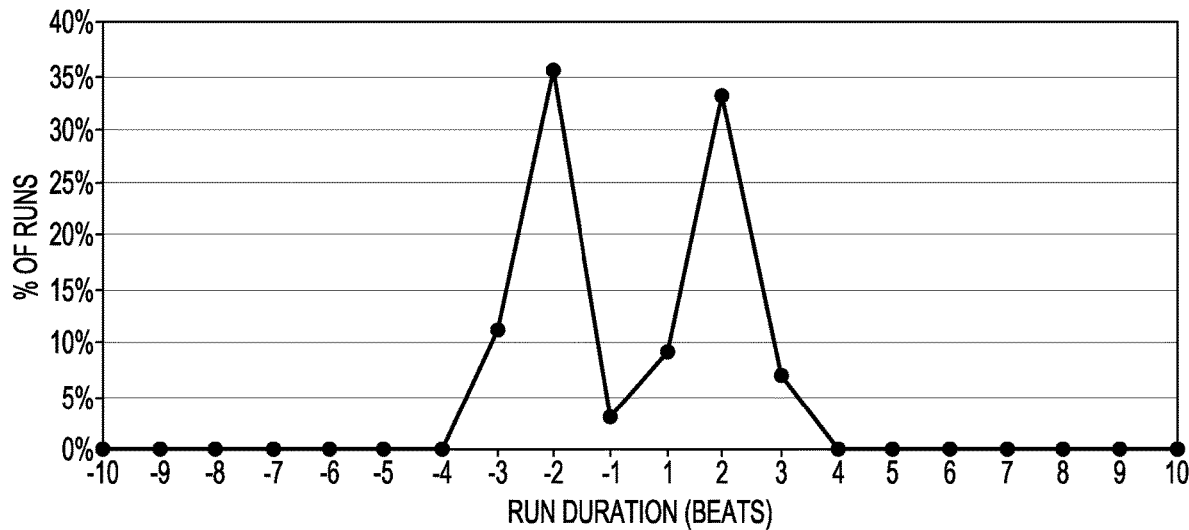
Figure 5E:
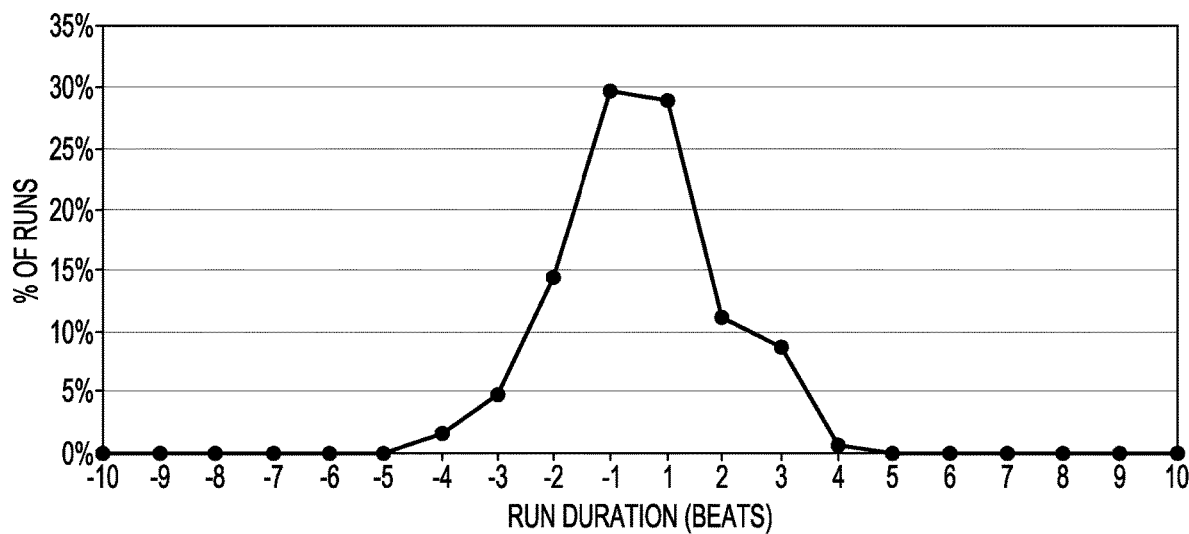
Figure 5F:
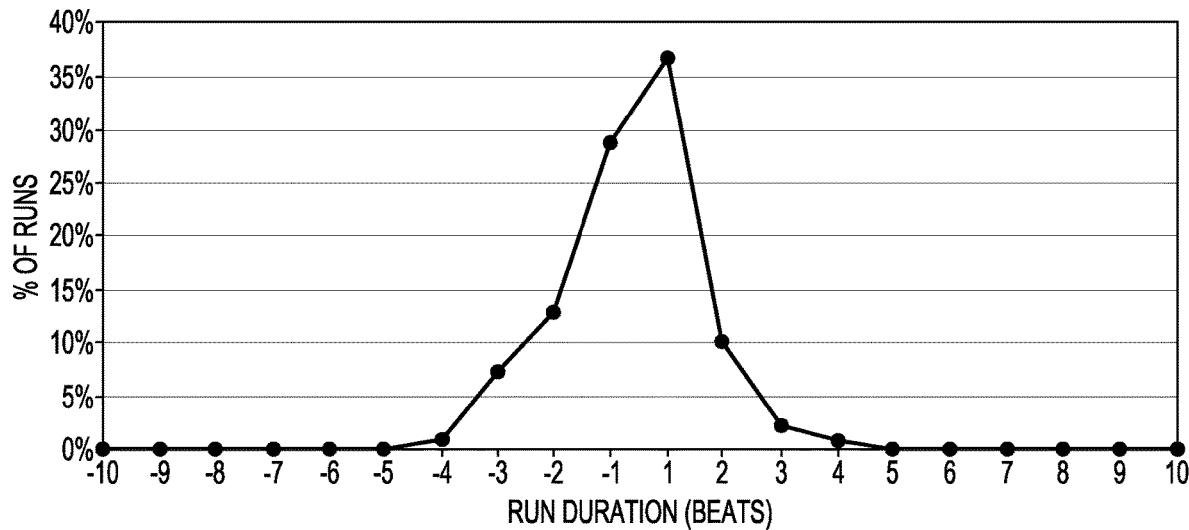
Figure 5G:
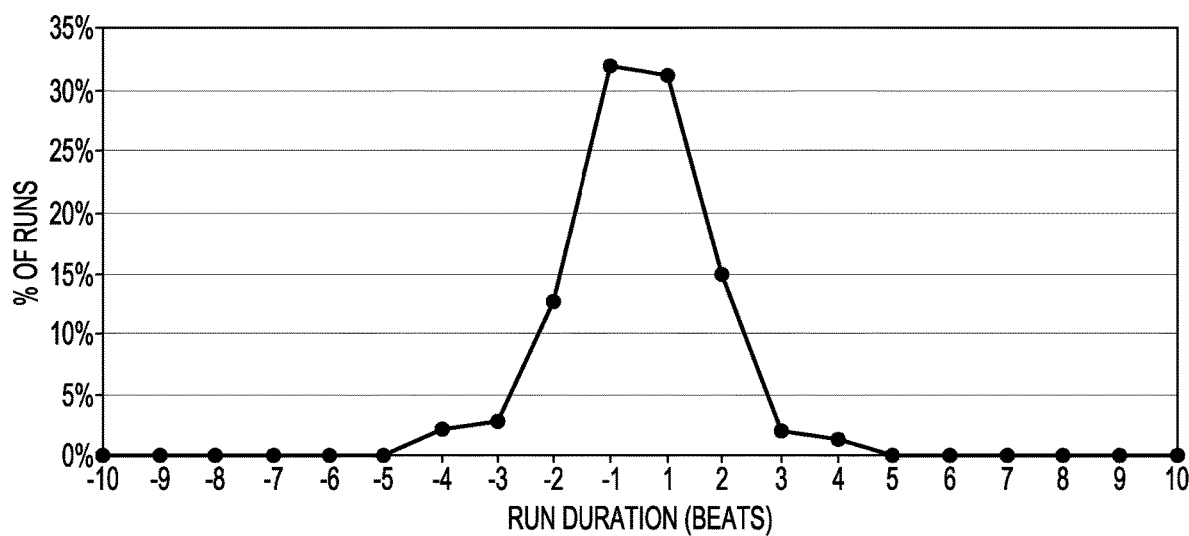

FIGS. 5B-F are histograms illustrating various examples of runs distribution in RSA detection using method 430. FIGS. 5B, 5C, and 5D show examples of the runs distribution during normal sinus rhythm when RSA is present. FIGS. 5E, 5F, and 5G show examples of the runs distribution during AF with no indication of RSA. It is noted that depending on the patient and various circumstances, RSA may not always be detectable using the statistical runs test, but when it is detected, it can be used to negate a false detection of AF.

In various embodiments, RSA detector 108 can include RSA detector 308 alone, one or more different RSA detectors each using a different method to detect the RSA, or a combination of RSA detector 308 and the one or more different RSA detectors. Step 215 of method 210 can be performed using method 430 alone, one or more different methods for detecting RSA, or a combination of method 430 and the one or more different methods. In various embodiments, AF can be detected using the ventricular rate variability and/or any other method. The verification of detection of AF based on whether RSA is present is not dependent on the specific method used for detecting the AF.

Figure 6:
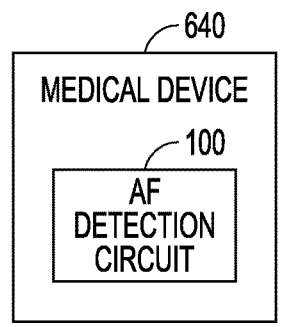
FIG. 6 is a block diagram illustrating an embodiment of a medical device including the AF detection circuit of FIG. 1.

FIG. 6 is a block diagram illustrating an embodiment of a medical device 640 including AF detection circuit 100. While examples of medical device 640 include an implantable loop recorder (ILR) that senses one or more ventricular signals, a single-chamber ICD in which atrial electrogram is not sensed, diagnostic patches or wearable devices that sense surface ECGs, and subcutaneous devices that are implanted subcutaneously to sense cardiac activities, medical device 640 represent any medical device that detects AF using the detection and RSA-based verification as discussed in this document.

In various embodiments, the circuit of medical device 640, including AF detection circuit 100, may be implemented using a combination of hardware and software. In various embodiments, each element AF detection circuit 100, including its various embodiments, may be implemented using an application-specific circuit constructed to perform one or more particular functions or a general-purpose circuit programmed to perform such function(s). For example, detector 104 and detection enhancer 106 (including RSA detector 108) may each be implemented using an application-specific circuit constructed to perform one or more functions discussed as method(s) or method step(s) in this document or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 7:
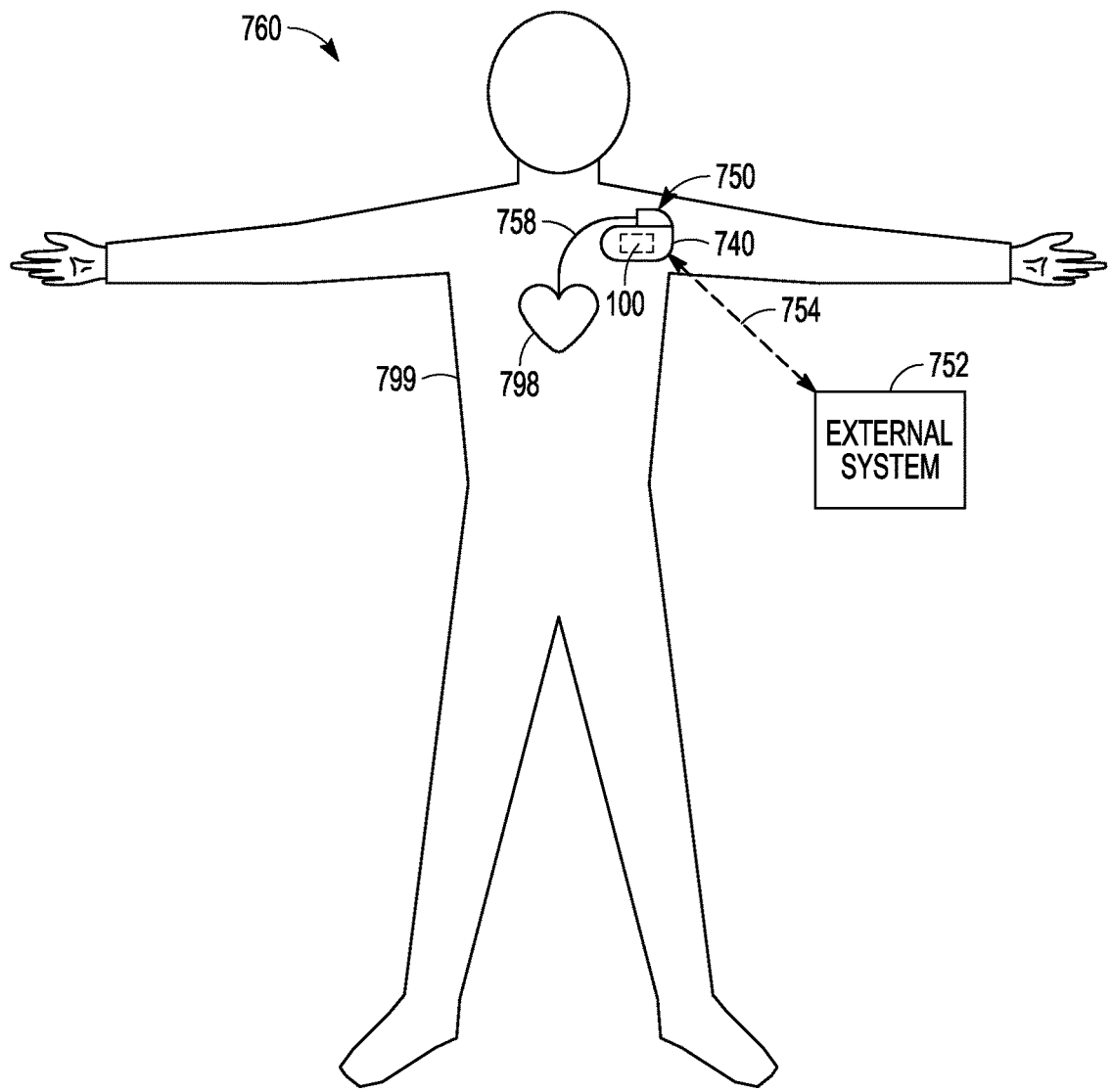
FIG. 7 is an illustration of an embodiment of a cardiac rhythm management (CRM) system and portions of an environment in which the system operates.

FIG. 7 is an illustration of an embodiment of a cardiac rhythm management (CRM) system 760 and portions of an environment in which system 760 operates. System 760 includes an implantable system 750, an external system 752, and a telemetry link 754 providing for communication between implantable system 750 and external system 752.

Implantable system 750 includes, among other things, implantable medical device 740 and lead system 758. In various embodiments, implantable medical device 740 is an implantable CRM device including one or more of a cardiac monitor, a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 7, implantable medical device 740 is implanted in a patient's body 799. In various embodiments, lead system 758 includes leads for sensing physiological signals and delivering pacing pulses, cardioversion/defibrillation shocks, neurostimulation pulses, pharmaceutical agents, biological agents, and/or other types of energy or substance for treating cardiac disorders. In one embodiment, lead system 758 includes one or more pacing-sensing leads each including at least one electrode placed in or on the patient's heart 798 for sensing electrogram and/or delivering pacing pulses. In other embodiments, electrodes placed in body 799 but away from heart 798 are used to sense physiological signals and deliver pacing pulses, cardioversion/defibrillation shocks, neurostimulation pulses, pharmaceutical agents, biological agents, and/or other types of energy or substance for treating cardiac disorders. In a specific embodiment, one or more electrodes are incorporated onto implantable medical device 740 for subcutaneous placement.

Implantable medical device 740 includes AF detection circuit 100 for detecting AF. In various embodiments, implantable medical device 740 adjusts the delivery pacing pulses, cardioversion/defibrillation shocks, neurostimulation pulses, pharmaceutical agents, biological agents, and/or other types of energy or substance for treating cardiac disorders in response to each detection of the AF. For example, implantable medical device 740 may be configured to deliver CRT or another therapy treating heart failure, determine AF burden being the percentage of time during which AF is indicated, and adjust the CRT and/or other therapy based on the AF burden. The other therapy may be delivered by implantable medical device 740 or using another means associated with or independent of implantable medical device 740.

In various embodiments, AF detection circuit 100 provides implantable medical device 740 with the capability of detecting AF. This eliminates the need to access an atrium for atrial tachyarrhythmia detection when the access is not otherwise required.

External system 752 allows the user and/or the patient to control the operation of implantable medical device 740 and obtain information acquired by implantable medical device 740. In one embodiment, external system 752 includes a programmer communicating with implantable medical device 740 bi-directionally via telemetry link 754. In another embodiment, external system 752 is a patient management system including an external device communicating with a remote device through a telecommunication network. The external device is within the vicinity of implantable medical device 740 and communicates with implantable medical device 740 bi-directionally via telemetry link 754. The remote device allows the user to monitor and treat the patient from a distant location.

Telemetry link 754 provides for data transmission from implantable medical device 740 to external system 752. This includes, for example, transmitting real-time physiological data acquired by implantable medical device 740, extracting physiological data acquired by and stored in implantable medical device 740, extracting therapy history data stored in implantable medical device 740, and extracting data indicating an operational status of implantable medical device 740 (e.g., battery status and lead impedance). Telemetry link 754 also provides for data transmission from external system 752 to implantable medical device 740. This includes, for example, programming implantable medical device 740 to acquire physiological data, programming implantable medical device 740 to perform at least one self-diagnostic test (such as for a device operational status), and programming implantable medical device 740 to deliver at least one therapy.

Figure 8:
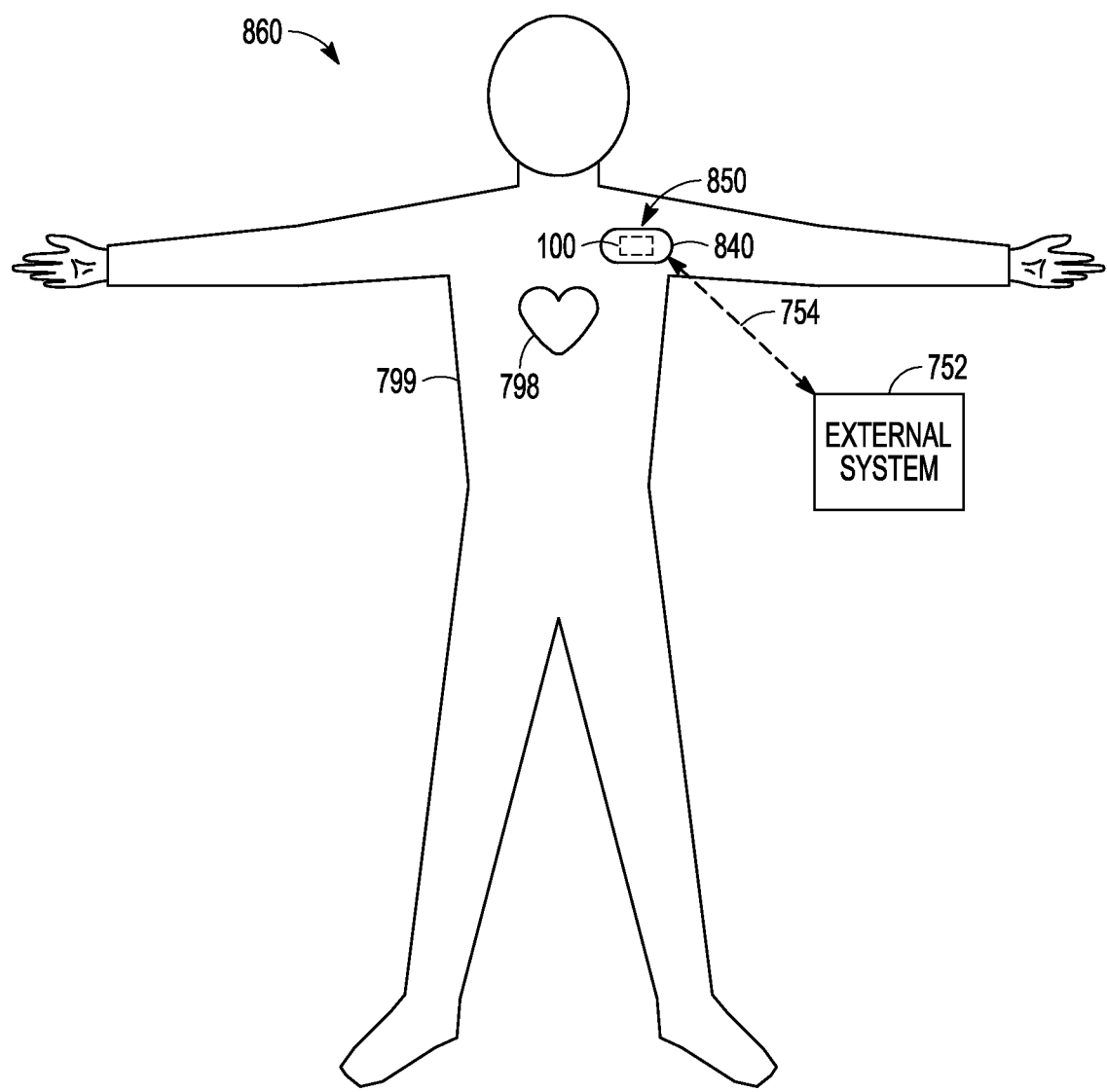
FIG. 8 is an illustration of another embodiment of a cardiac rhythm management system and portions of an environment in which the system operates.

FIG. 8 is an illustration of an embodiment of a CRM system 860 and portions of an environment in which system 860 operates. System 860 includes an implantable system 850, external system 752, and telemetry link 754 providing for communication between implantable system 850 and external system 752. Implantable system 850 differs from implantable system 750 in that it includes an implantable medical device 840 without a lead system. Implantable medical device 840 is a cardiac monitoring device that includes AF detection circuit 100 for the capability of detecting AF without a lead to provide electrical connection to heart 798. In various embodiments, implantable medical device 840 detects atrial arrhythmia and communicates indications of one or more specified types of atrial arrhythmias to external system 752 via telemetry link 754 on a continuous or periodic basis or upon request. Such indications provide a physician or other caregiver with information needed for treating the patient. For example, implantable medical device 840 may be configured to detect AF in a patient with heart failure. Implantable medical device 840 or external system 752 may be configured to determine the AF burden, which is then used as a basis for starting, stopping, or adjusting one or more therapies for treating the heart failure.

Figure 9:
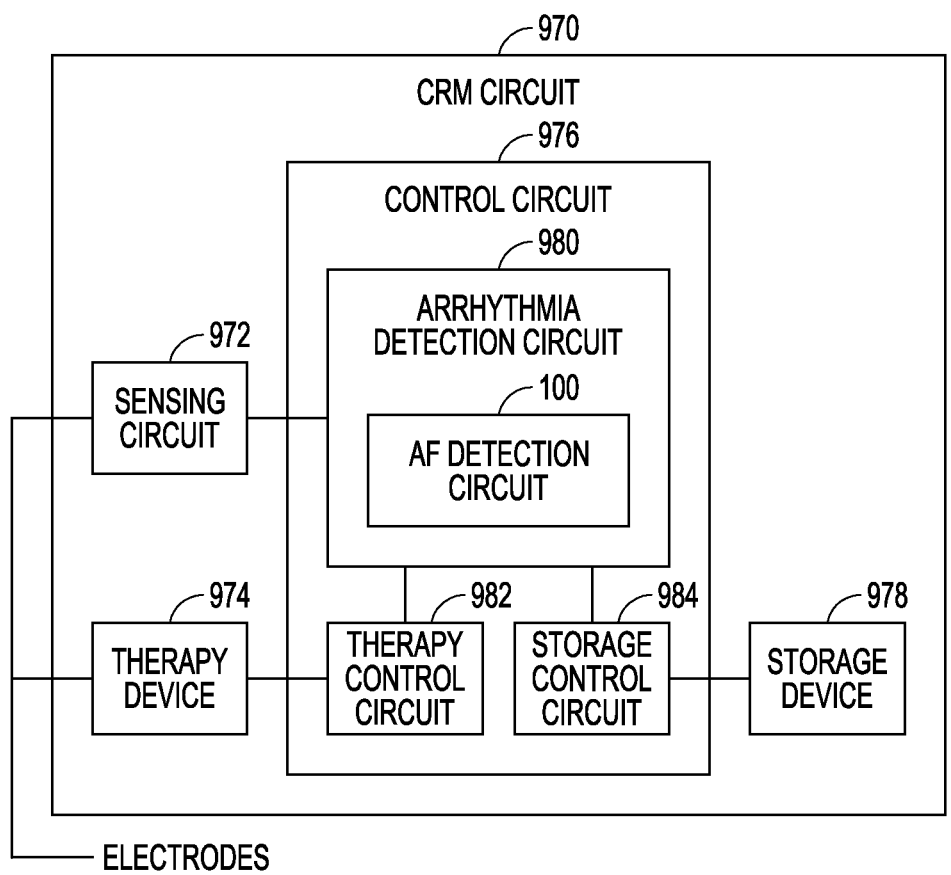
FIG. 9 is a block diagram illustrating an embodiment of a CRM circuit including the AF detection circuit of FIG. 1.

FIG. 9 is a block diagram illustrating an embodiment of a CRM circuit 970 that includes AF detection circuit 100. CRM circuit 970 can be an example of the circuit in implantable medical device 640, 740, or 840 and can be configured for use in any medical device that provides for CRM and detects AF. CRM circuit 970 can include a sensing circuit 972, a therapy device 974, a control circuit 976, and a storage device 978.

Sensing circuit 972 senses one or more cardiac signals indicative of atrial depolarizations (P-waves) and ventricular depolarizations (R-waves). Examples of such one or more cardiac signals include one or more electrocardiograms (ECGs), one or more subcutaneous ECGs, and one or more intracardiac electrograms (such as atrial and ventricular electrograms). Each of these signals can be an example of the cardiac signal from which AF and RSA can be detected, as discussed in this document.

Therapy device 974 delivers one or more therapies. Examples of such one or more therapies include a cardiac pacing circuit to deliver cardiac pacing pulses, a cardioversion/defibrillation circuit to deliver cardioversion/defibrillation shocks, a neurostimulation circuit to deliver neurostimulation pulses or other form of neurostimulation energy, a drug delivery device to deliver one or more drugs, and a biologic therapy device to deliver one or more biologic therapies. In various embodiments, the one or more therapies are each for treatment of AF and/or necessarily or preferably adjusted based on whether AF is detected.

Storage device 978 stores portions of the sensed one or more cardiac signals. In various embodiments, storage device 978 also stores various control algorithms used by control circuit 976 as well as other signals acquired by CRM circuit 970. In various embodiments, only data associated with verified detection of AF are stored.

Control circuit 976 controls the operation of CRM circuit 970 and can include an arrhythmia detection circuit 980, a therapy control circuit 982, and a storage control circuit 984. Arrhythmia detection circuit 980 detects one or more types of cardiac arrhythmias using the one or more cardiac signals and includes an AF detection circuit 100 to detect AF using at least one of the one or more cardiac signals. Therapy control circuit 982 controls the delivery of the one or more therapies from therapy device 974 using the one or more cardiac signals. In various embodiments, therapy control circuit 982 starts, stops, or adjusts the delivery of a therapy of the one or more therapies in response to a detection of a type of arrhythmia of the one or more types of cardiac arrhythmias. In various embodiments, therapy control circuit 982 controls the delivery of the one or more therapies based on whether AF is detected and verified, and can be configured to start, stop, or adjust the delivery of a therapy of the one or more therapies in response to a verified detection of AF. Storage control circuit 978 starts storage of the one or more cardiac signals in response to a detection of a type of arrhythmia of the one or more types of cardiac arrhythmias. In one embodiment, storage control circuit 978 stops the storage of the one or more cardiac signals when the type of arrhythmia is no longer detected. In various embodiments, storage control circuit 978 starts storage of the one or more cardiac signals in response to a verified detection of AF and stops the storage when the AF is no longer detected or verified.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
a sensing circuit configured to sense a cardiac signal indicative of atrial and ventricular depolarizations; and
an atrial fibrillation (AF) detection circuit configured to detect AF using the cardiac signal, the AF detection circuit including:
a detector configured to detect the ventricular depolarizations using the cardiac signal, to measure ventricular intervals each between two successively detected ventricular depolarizations, and to detect the AF using the ventricular intervals; and
a detection enhancer including a respiratory sinus arrhythmia (RSA) detector configured to detect RSA using the cardiac signal, the detection enhancer configured to verify each detection of the AF based on whether the RSA is detected.

2. The system of claim 1, wherein the detector is configured to compute a measure of ventricular rate variability using the ventricular intervals and to indicate a suggested detection of the AF in response the measure of ventricular rate variability satisfying one or more criteria for the AF, and the detection enhancer is configured to indicate a detection of the AF in response to the suggested detection of the AF being indicated while the RSA is not detected.

3. The system of claim 1, wherein the detection enhancer is configured to negate a detection of the AF when the RSA is detected.

4. The system of claim 1, wherein the detection enhancer is configured to indicate a false positive detection of the AF when the AF is detected by the detector while the RSA is detected.

5. The system of claim 1, wherein the RSA detector comprises:
a runs detector configured to detect runs of consecutively faster heart beats and consecutively slower heart beats from the cardiac signal over a period; and
a runs analyzer configured to analyze the detected runs for an RSA pattern and to declare a detection of the RSA in response to the RSA pattern being present.

6. The system of claim 5, wherein the runs analyzer is configured to produce a histogram of percentage of runs at each run duration of run durations each specified by a number of heart beats per run.

7. The system of claim 6, wherein the runs analyzer is configured to detect the RSA pattern including at least one of a low percentage of 1-beat runs or an increasing number of multiple-beat runs as the number of beats in each of the multiple-beat runs increases.

8. The system of claim 1, comprising an implantable medical device including:
the sensing circuit;
the AF detection circuit;
a therapy device configured to deliver one or more therapies; and
a therapy control circuit configured to control the delivery of the one or more therapies based on whether the each detection of the AF is verified.

9. The system of claim 8, wherein the sensing circuit is configured to sense a subcutaneous electrocardiogram.

10. The system of claim 1, further comprising:
a storage device configured to store portions of the sensed cardiac signal; and
a storage control circuit configured to start storage of a portion of the portions of the sensed cardiac signal in response to the each detection of the AF being verified.

11. A method, comprising:
sensing a cardiac signal indicative of atrial and ventricular depolarizations;
detecting the ventricular depolarizations using the cardiac signal;
measuring ventricular intervals each between two successively detected ventricular depolarizations;
detecting atrial fibrillation (AF) using the ventricular intervals;
detecting respiratory sinus arrhythmia (RSA) using the cardiac signal; and
verifying each detection of the AF based on whether the RSA is detected.

12. The method of claim 11, wherein detecting the AF using the ventricular intervals comprises:
computing a measure of ventricular rate variability using the ventricular intervals; and
indicating a suggested detection of AF in response the measure of ventricular rate variability satisfying one or more criteria for AF,
and verifying the each detection of the AF comprises indicating a detection of the AF in response to the suggested detection of the AF being indicated while the RSA is not detected.

13. The method of claim 11, further comprising negating a detection of the AF when the RSA is detected.

14. The method of claim 11, further comprising indicating a false positive detection of the AF when the AF is detected by the detector while the RSA is detected.

15. The method of claim 11, further comprising triggering storage of the sensed cardiac signal in response to the each detection of the AF being verified.

16. The method of claim 11, wherein detecting the RSA comprises:
detecting runs of consecutively faster heart beats and consecutively slower heart beats from the cardiac signal over a period;
analyzing the detected runs for an RSA pattern; and
declaring a detection of the RSA in response to the RSA pattern being present.

17. The method of claim 16, wherein analyzing the detected runs for the RSA pattern comprises:
producing a histogram of percentage of runs at each run duration of run durations each specified by a number of heart beats per run; and
detecting the RSA pattern including at least one of a low percentage of 1-beat runs or an increasing number of multiple-beat runs as the number of beats in each of the multiple-beat runs increases.

18. The method of claim 11, wherein sensing the cardiac signal comprises sensing a subcutaneous electrocardiogram from a site remote from a heart.

19. The method of claim 11, further comprising:
delivering one or more therapies; and
controlling the delivery of the one or more therapies based on whether the each detection of the AF is verified.

20. The method of claim 19, wherein delivering the one or more therapies comprises delivering at least one of the one or more therapies from an implantable medical device.

* * * * *